Dec. 6, 1966 D. L. ARMSTRONG ETAL Plant Pat. 2,688
ROSE PLANT
Filed Oct. 22, 1965
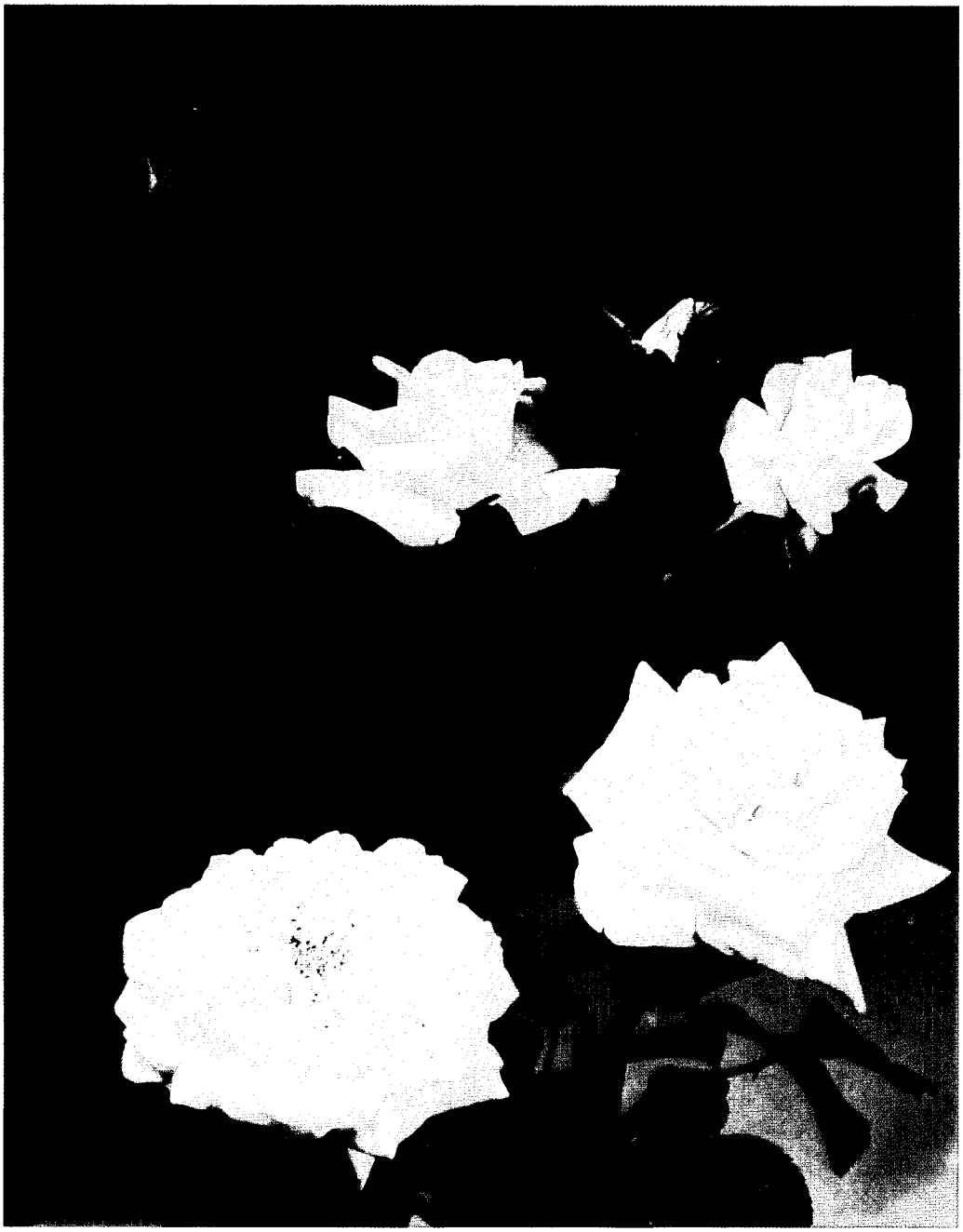
Inventors.
D. L. Armstrong
H. C. Swim
By: Robb & Robb
Attorneys.

United States Patent Office

Plant Pat. 2,688

Patented Dec. 6, 1966

2,688

ROSE PLANT

David L. Armstrong and Herbert C. Swim, both of Ontario, Calif., assignors to Armstrong Nurseries, Inc., Ontario, Calif., a corporation of California Filed Oct. 22, 1965, Ser. No. 502,786
1 Claim. (Cl. Plt.—14)

The present invention relates to a new and distinct variety of rose plant of the hydbrid tea class, which was orignated by us by crossing the variety "Buccaneer" (Plant Patent No. 1,119) with the variety "Cherry Glow" (Plant Patent No. 1,490), the variety "Buccaneer" being the seed parent and the variety, "Cherry Glow" being the pollen parent.

The general objective of this breeding was to produce new and improved varieties of roses which bear flowers in a variety of colors. The present variety is one of the resulting achievements, as evidenced by the following unique combination of characteristics which are outstanding therein and which distinguish it from its parents, as well as from all other varieties of which we are aware:

(1) A very vigorous and upright plant habit which is particularly good for a white-flowered rose variety;

(2) Large, attractive, leathery and semiglossy dark green foliage;

(3) An excellent urn-shaped bud form which holds up very well under most weather conditions;

(4) Double flowers of from medium to large size which are borne on strong stems ranging from medium length to long; and (5) A distinctive and attarctive white flower color which has a trace of pale yellow.

In comparison with its seed parent "Buccaneer," the flower color of the new variety is near white, whereas that of this parent is yellow.

As compared with its pollen parent "Cherry Glow," the flowers of the now variety have considerably more petals, and the flower color is near white instead of red like the flowers of this parent.

A sexual reproduction of our new variety by budding, as performed at Ontario, California, shows that the foregoing characteristics and distinctions come true to form and are established and transmitted through succeeding propagations.

The accompanying drawing shows typical specimens of the vegetative growth and flowers of our new variety in different stages of development, with some of the flowers and vegetative growth being depicted in color as nearly true as it is reasonably possible to make the same in a color illustration of this character.

The following is a detailed description of the new variety, with color terminology in accordance with Robret F. Wilson's Horticultural Colour Chart (hereinafter abbreviated as (W)) and Robert Ridgway's Color Standards and Nomenclature (hereinafter abbreviated as (R)), as indicated:

Type: Tall; bush; outdoor; seedling; for cut flowers and for garden decoration.

Class: Hybrid tea.

Breeding: Seedling.

*Seed parent.*—"Buccaneer."

*Pollen parent.*—"Cherry Glow."

Propagation: Holds its distinguishing characteristics through succeeding propagations by budding.

*Flower*

Locality where grown and observed: Ontario, California.

Flowers borne: Sometimes singly, but sometimes from 2 to 5 to stem; in irregular clusters; on strong stems ranging from medium length to long.

Quantity of bloom: Abundant, outdoors.

Continuity: Nearly continuous during growing season.

Fragrance: From slight to moderate.

Bud:

*Peduncle.*—From average lingth to long; from average caliper to heavy; erect; usually smooth; with several to many stipitate glands and several to many small prickles. Color—between Biscay Green, Plate XVII (R) and Apple Green, Plate XVII (R).

*Before calyx breaks.*—Size—from medium to large. Form—from medium length to long; pointed and ovoid.

*As calyx breaks.*—Color—between Dresden Yellow, Plate 64/2, page 64 (W) and Chartreuse Green, Plate 663/2, page 90 (W).

*Sepals.*—Inner surface—with fine, wooly tomentum. Outer surface—with many small stipitate glands. Alternate margins—lined with fine, wooly tomentum. Other margins—with many small stipitate glands and small slender foliaceous parts, also lined with small stipitate glands; sepals usually with foliaceous appendages extending from ⅓ to ½ sepal length.

*As first petal opens.*—Size—from average to large. Form—long; from ovoid to urn-shaped. Color: Outside—between Primrose Yellow, Plate 601/3, page 65 (W) and Chartreuse Green, Plate 663/3, page 90 (W), and blending with near Dresden Yellow, Plate 64/2, page 64 (W) toward base of petal; inside—same as outside.

*Opening.*—Opens up well; is not retarded or prevented from opening by cold, hot, wet or dry weather.

Bloom:

*Size (when fully open).*—From average to large; from 4½ inches to 5½ inches.

*Petalage.*—From 35 to 45 petals, plus 8 to 12 petaloids; arranged irregularly.

*Form.*—High-centered at first but becoming cupped to high-centered; petals being at first tightly cupped with tips reflexed outward, but later becoming more loosely cupped, with tips reflexed outward at maturity; outside petals of newly opened flowers usually reflexed outward along both edges and apex; outside and intermediate petals of three-days open flower usually reflexed outward along both edges and apex.

Petals:

*Texture.*—Moderately leathery.

*Appearance.*—Inside—satiny. Outside—satiny.

*Shape.*—Outside—between round and broadly obovate, with apex flat and sometimes with 1 or 2 notches. Intermediate—obovate, with apex from rounded to flat and sometimes with 1 or 2 notches. Inside—obovate, with apex rounded and sometimes with 1 or 2 notches.

This description of a newly opened flower was made from a rose grown outdoors during the month of September at Ontario, California:

*Color.*—Outer petal: Outside surface—near white, blending with near Dresden Yellow, Plate 64/2, page 64 (W) toward base of petal; inside surface—near white, blending with near Dresden Yellow, Plate 64/1, page 64 (W) toward base of petal. Intermediate petal: Outside surface—near Chartreuse Green, Plate 663/3, page 90 (W), blending with near Dresden Yellow, Plate 64/2, page 64 (W) toward base of petal; inside surface—between Primrose Yellow, Plate 601/3, page 65 (W) and Chartreuse Green, Plate 663/3, page 90 (W), blending with near Dresden Yellow, Plate 64/1, page 64 (W) toward base of petal. Inner petal: Outside surface—same as outside surface of intermediate petal; inside surface—between Primrose Yellow, Plate 601/3, page 65 (W) and Chartreuse Green, Plate 663/3, page 90 (W), blending with near Dresden Yellow, Plate 64, page 64 (W) toward base of petal.

This description was made from rose that was open for three days outdoors during the month of September at Ontario, California:

*Color.*—Outer petal: Outside surface—near white, with area toward base of petal shaded very lightly with near Dresden Yellow, Plate 64/3, page 64 (W); inside surface—same as outside surface. Inner petal: Outside surface—between white and Dresden Yellow, Plate 64/3, page 64 (W), blending with near Dresden Yellow, Plate 64/2, page 64 (W) toward base of petal; inside surface—same as outside surface.

*General color effect.*—Newly opened flower—between white and Chartreuse Green, Plate 663/3, page 90 (W), with center of flower near Primrose Yellow, Plate 601/2, page 65 (W). 3-days open—near white, with center of flower shaded near Dresden Yellow, Plate 64/3, page 64 (W).

*Behavior.*—Drop off cleanly; not particularly affected by cold, hot, wet or dry weather.

*Flower longevity.*—On bush in garden 4 or 5 days in October. Cut roses grown outdoors and kept at livingroom temperatures—4 or 5 days in October.

*Reproductive organs*

Stamens: From average number to many; arranged regularly about pistils; a few mixed with petaloids.

Filaments: From medium length to long (from 6 mm. to 15 mm.); most with anthers. Color—near Lemon Yellow, Plate 4/2, page 4 (W).

Anthers: Medium size; all open approximately at once. Color: Upper side—margins near Tangerine Orange, Plate 9/1, page 9 (W), with remainder near Canary Yellow, Plate 2/2, page 2 (W); under side—same as upper side.

Pollen: Moderate abundance. Color—near Tangerine Orange, Plate 9, page 9 (W).

Pistils: Average number (approximately 80).

Styles: Moderately even; short; thin; bunched. Color—upper ¼ of style near Chrome Yellow, Plate 605/1, page 144 (W), with remainder near Dresden Yellow, Plate 64/3, page 64 (W).

Stigma: Color—near Lemon Yellow, Plate 4/1, page 4 (W).

Ovaries: Usually all enclosed in calyx.

Hips: Between short and average length; usually globular; smooth; walls thick and fleshy. Color (half mature)—near Absinthe Green, Plate XXXI (R).

Sepals: Fall soon; from medium length to long; straight. Color: Inside—near Vetiver Green, Plate XLVII (R); outside—near Rainette Green, Plate XXXI (R).

Seeds: From few to average number (from 8 to 20); from small to medium size.

*Plant*

Foliage:

*Leaves.*—Compound of usually 3 to 7 leaflets; abundant; large; leathery; semi-glossy.

*Leaflets.*—Shape—between round and oval, with apex acute. Base—round. Margin—simply serrate.

*Color.*—Mature: Upper surface—between Forest Green, Plate XVII (R) and Deep Dull Yellow-Green (2), Plate XXXII (R); under surface—near Chromium Green, Plate XXXII (R). Young: Upper surface—near Light Cress Green, Plate XXXI (R); under surface—near Rainette Green, Plate XXXI (R) overlaid with near Prussian Red, Plate XXVII (R).

*Rachis (the supporting stem of the compound leaf).*—From average size to heavy. Upper side—grooved; with few to several stipitate glands on edges. Under side—smooth; with none to few small prickles.

*Stipules.*—Medium length; from medium width to wide; with short to medium length points turning out at an angle of more than 45°.

*Disease resistance.*—Better than average resistance to mildew, as compared with other rose varieties grown under comparable cultural conditions at Ontario, California.

Growth:

*Habit.*—Upright and moderately branched.

*Growth.*—Very vigorous.

*Canes.*—Heavy.

*Main stems.*—Color—near Biscay Green, Plate XVII (R). Large prickles—several; from medium length to long; hooked slightly downward; with long, broad base; color—near Wood Brown, Plate XL (R). Small prickles—from few to several; color—near Wood Brown, Plate XL (R). Hairs—none.

*Branches.*—Color—near Chromium Green, Plate XXXII (R). Large prickles—from several to many; medium length; hooked downward slightly; with narrow base of medium length; color—near Walnut Brown, Plate XXVIII (R). Small prickles—few; color—near Walnut Brown, Plate XXVIII (R). Hairs—none.

*New shoots.*—Color—near Apple Green, Plate XVII (R), overlaid with near Cameo Brown, Plate XXVIII (R) on areas exposed to the sun. Large prickles—few; from medium length to long; hooked slightly downward; with long, narrow base of medium length; color—near Mineral Red, Plate XXVII (R). Small prickles—few; color—near Mineral Red, Plate XXVII (R). Hairs—none.

We claim:

A new and distinct variety of rose plant of the hybrid tea class, substantially as herein shown and described, characterized particularly as to novelty by the unique combination of a very vigorous and upright plant habit which is particularly good for a white-flowered rose variety, large, attractive, leathery and semi-glossy dark green foliage, an excellent urn-shaped bud form which holds up very well under most weather conditions, double flowers of from medium to large size which are borne on strong stems ranging from medium length to long, and a distinctive and attractive white flower color which has a trace of pale yellow.

No references cited.

ABRAHAM G. STONE, *Primary Examiner.*

R. E. BAGWILL, *Assistant Examiner.*